(12) United States Patent
Kapre

(10) Patent No.: US 9,452,213 B2
(45) Date of Patent: Sep. 27, 2016

(54) GENETICALLY DETOXIFIED PERTUSSIS VACCINE THAT MAINTAINS INTRINSIC ADJUVANT ACTIVITY

(71) Applicant: Subhash V. Kapre, Redmond, WA (US)

(72) Inventor: Subhash V. Kapre, Redmond, WA (US)

(73) Assignee: Inventprise, LLC, Redmond, WA (US)

(*) Notice: Subject to any disclaimer, the term of this patent is extended or adjusted under 35 U.S.C. 154(b) by 0 days.

(21) Appl. No.: 14/800,126

(22) Filed: Jul. 15, 2015

(65) Prior Publication Data

US 2016/0015806 A1    Jan. 21, 2016

Related U.S. Application Data

(60) Provisional application No. 62/024,577, filed on Jul. 15, 2014.

(51) Int. Cl.
  *A61K 39/39* (2006.01)
  *A61K 39/02* (2006.01)
  *A61K 39/00* (2006.01)

(52) U.S. Cl.
  CPC ............. *A61K 39/39* (2013.01); *A61K 39/099* (2013.01); *A61K 2039/55544* (2013.01); *A61K 2039/55572* (2013.01); *C12Y 406/01001* (2013.01)

(58) Field of Classification Search
  CPC ............... A61K 2039/55572; A61K 39/0018; A61K 39/04; A61K 39/07; A61K 39/095; A61K 39/102; A61K 39/145; A61K 39/21; A61K 39/245; A61K 39/25; A61K 39/29; A61K 39/292; A61K 39/39; C12N 2710/16634; C12N 2710/167
  See application file for complete search history.

(56) References Cited

U.S. PATENT DOCUMENTS

| 2001/0018056 A1 | 8/2001 | Roberts |
| 2007/0116711 A1 | 5/2007 | Castado et al. |
| 2009/0317854 A1 | 12/2009 | Leclerc et al. |
| 2012/0064084 A1 | 3/2012 | Matsumoto |
| 2013/0273101 A1 | 10/2013 | Cho et al. |

OTHER PUBLICATIONS

Search Report and Written Opinion for PCT App. No. PCT/US15/40574 dated Oct. 23, 2015.

*Primary Examiner* — Padma V Baskar
(74) *Attorney, Agent, or Firm* — Remenick PLLC

(57) ABSTRACT

The invention is directed to a method for the production of a *pertussis* vaccine and, in particular, a detoxified *pertussis* vaccine comprising detoxified *pertussis* toxin (PT), detoxified *pertussis* lipopolysaccharide (P-LPS), and detoxified *pertussis* adenylate cyclase toxin (P-ACT). The invention is also directed to the manufacture of a vaccine or the invention and methods for the administration of a detoxified vaccine to patients.

18 Claims, 1 Drawing Sheet

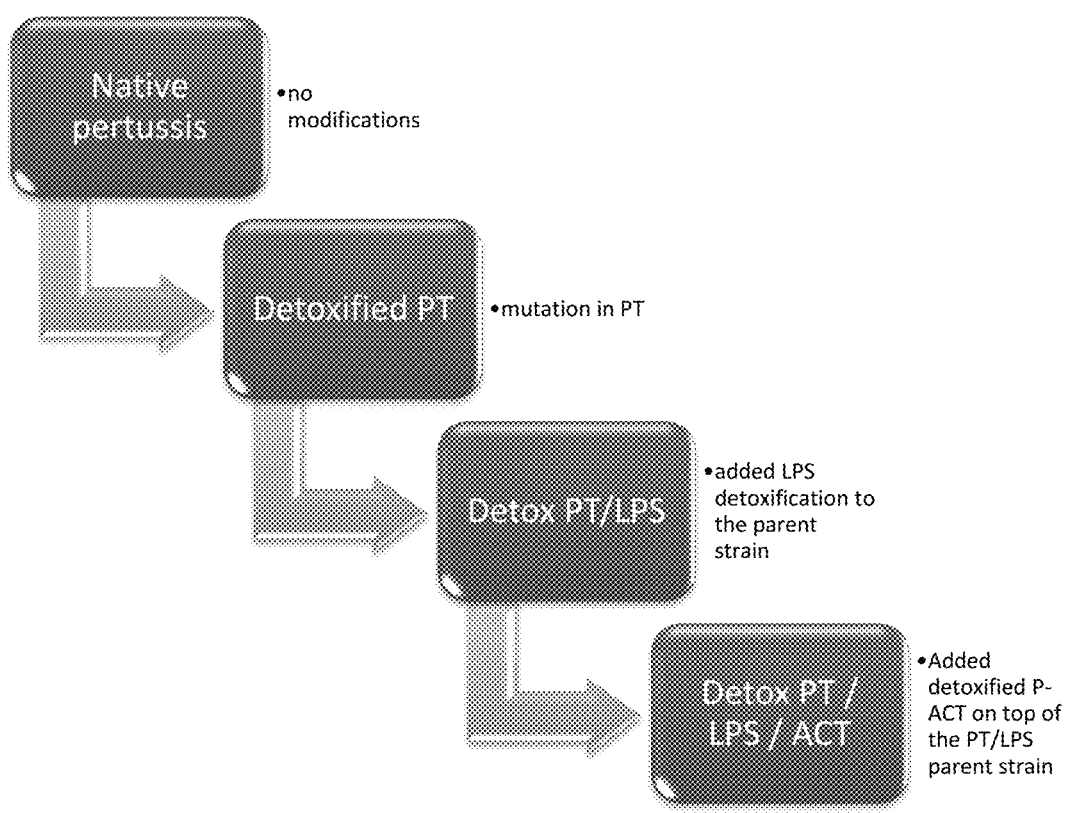

GENETICALLY DETOXIFIED PERTUSSIS VACCINE THAT MAINTAINS INTRINSIC ADJUVANT ACTIVITY

REFERENCE TO RELATED APPLICATIONS

This application claims priority to U.S. Provisional Application No. 62/024,577 of the same title and filed Jul. 15, 2014, the entirety of which is hereby incorporated by reference.

BACKGROUND

1. Field of the Invention

The invention is directed to methods for the production and manufacture of vaccines for the treatment or prevention of infection due to *Bordetella pertussis* and, in particular, the invention is directed to a detoxified *pertussis* vaccine and methods for the administration of detoxified vaccines to patients.

2. Description of the Background

The bacterium *Bordetella pertussis* is the most common causative agent for the disease referred to as whooping cough. Whooping cough is a respiratory disease that can infect both adults and children. Although treatable with antibiotics, it can be a serious disease for infants especially. Clinically the disease is characterized by paroxysms of rapid coughs followed by inspiratory effort, often associated with a characteristic 'whooping' sound—thus the name. In more serious cases, there can be pneumonia and complications caused by pneumonia, and also brain oxygen deprivation which can lead to brain damage and death.

Although most often due to *B. pertussis*, about 5-10% of cases of whooping cough may be caused by a serologically related microorganism (e.g., *B. parapertussis*) (see, Mertsola (1985) Eur J Clin Microbiol 4; 123; Lautrop (1971) Lancet 1(7711) 1195-1198). Infections due to *B. parapertussis* are clinically mild as compared with *B. pertussis* and, due to the cross reactivity with *B. pertussis* makes *B. parapertussis* difficult to diagnose as the causative agent.

The first generation of vaccines against *B. pertussis* were whole cell vaccines (referred to as wP vaccines), composed of bacteria which were treated with chemicals such as formaldehyde to kill the cells and inactivate the toxic materials. Highly efficacious, these vaccines were introduced in many countries in the 1950s and 1960s. Although successful at reducing incidence of whooping cough, a major problem with wP vaccines was the high level of reactogenicity, which commonly included the side effect of fever and local reactions.

The need for a more defined vaccine was recognized which led to the development of a vaccine comprising lesser number of highly purified antigens from different microorganisms. The result was what was generally referred to as the component vaccine and contains immunogenic portions of diphtheria, tetanus and *pertussis* (DTP). Initial DTP vaccines contained *pertussis* endotoxin, surface lipooligosaccharide (LOS) of *B. Pertussis* (DTwP vaccines). LOS is a low molecular weight form of bacterial lipopolysaccharides (LPS). Although effective, these vaccines produced a number of deleterious side effects.

In the 1990's, newer *pertussis* vaccines were developed that, although less uniformly immunogenic, include only a few selected *pertussis* antigens, namely toxins and adhesins of *B. pertussis*. Although less defined as compared to component vaccines, these acellular vaccines (DTaP vaccines) are less likely to provoke side effects and have been approved by the FDA for administration to adults and children. Vaccines have been developed recently, also for administration to adults and children, which combine the tetanus and diphtheria toxoids with acellular *pertussis* vaccine. These (Tdap) vaccines, although less immunogenic than wP vaccines, contain reduced amounts of *pertussis* antigens compared to DTaP vaccines and, thus, have fewer side effects. Acellular vaccines containing purified *B. pertussis* proteins were less reactogenic and have been adopted for many vaccination programs around the world. Acellular vaccines typically containing *pertussis* toxin (PT), filamentous haemagglutinin (FHA) and quite often pertactin (PRN), are widely used and provide effective protection from the severity of whooping cough.

Despite vaccination, whooping cough remains an endemic disease (Mooi et al (2001) Emerging Infectious Diseases 7; 526), and has re-emerged in Australia, Canada and various areas of Europe; countries with highly vaccinated populations. A comparison of pre-vaccination strains with strains isolated from these areas has shown antigenic drift, particularly in PT and PRN (Mooi et al (1998) Infection and Immunity 66; 670). It has become accepted that current vaccinations protect against severe disease, but do not eliminate the *B. pertussis* infection (Cherry et al (1998) Vaccine 16; 1901, Hewlett and Halperin (1998) Vaccine 16; 1899, Storsaeter et al (1998) Vaccine 16; 1907). The defense mechanisms associated with *B. pertussis* allow the organism to escape the immunological processes that would otherwise destroy the microorganism.

Not surprisingly, vaccination using whole cell *B. pertussis* vaccines (Pw) have been shown to be protective against *B. parapertussis* infection as well, most likely due to an immunological similarity of the organisms. *B. parapertussis* infection in unvaccinated infants may lead to severe and fatal complications, whereas in individuals vaccinated with Pw, a milder, often subclinical course of whooping cough is seen (Long et al (1990) Pediatric Infect Dis J 9; 700). Thus, acellular *pertussis* vaccines containing only two or three purified proteins should reduce the ability of vaccination to protect against *B. parapertussis*. Further improved acellular vaccines against whooping cough are required that combine low reactogenicity with an ability to elicit a protective response against *Bordetella*, particularly with regard to infections of *B. pertussis* and *B. parapertussis*.

Thus, a need currently exists for an effective *pertussis* vaccine that is uniformly immunogenic and protective against infection that has few or no side effects.

SUMMARY OF THE INVENTION

In general, the invention is directed to vaccines and methods for making and administering vaccines that are effective against *pertussis*.

One embodiment of the invention is directed to vaccines for the treatment or prevention of an infection in a mammal comprising: a detoxified *pertussis* toxin protein; an enzyme treated LPS; and a detoxified adenylate cyclase protein. Preferably the vaccine is for the treatment or prevention of the infection of *B. pertussis*. Preferably the detoxified *pertussis* protein contains a mutation in one or more of subunits S1-S6 of *B. pertussis*, such as, for example, a substitution in S1 of glutamic acid for glycine at amino acid position 129 and a substitution of arginine for lysine at amino acid position 9. Preferably enzyme treated LPS comprises LPS treated with one or more alkaline phosphatases or one or more deacylases and the one or more phosphorylaese comprise Antarctic phosphatase or lambda protein phosphatase.

Also preferably, the detoxified adenylate cyclase protein comprised a dipeptide inserted between amino acids 188 and 189 of native P-ACT. Preferably the vaccine further comprises a pharmaceutically acceptable carrier such as, for example, water, glycerol, alcohol, propylene glycol, fatty alcohols, triglycerides, fatty acid esters, mineral oils, liquid petrolatum, isopropylpalmitate, polyethylene ethanol, polyoxyethylene monolauriater, sodium lauryl sulfate, an antioxidant, a humectant, a viscosity stabilizer or modifier, a colorant or a flavoring agent. Preferably the vaccine produces no side effects, such as, for example, no fever or inflammation at the site of administration to the individual.

Another embodiment of the invention is directed to methods of treating or preventing an infection comprising administering a therapeutically effective amount of the vaccine of the invention to a mammal. Preferably the infection is caused by one or more of *B. pertussis, B. parapertussis* or a serotype or strain of *B. pertussis* or *B. parapertussis*, and the vaccine comprises a detoxified *pertussis* toxin protein; an enzyme treated LPS; and a detoxified adenylate cyclase protein. Preferably administering is via injection, intramuscular injection, intravenous injection, oral administration, nasal administration, or a combination thereof. Preferably administration may be as a liquid, a tablet, a pill or a spray. Preferably the therapeutically effective dose is an amount of vaccine which produces an immune response in the mammal that is protective against and/or treats the infection. The therapeutically effective dose may be from about 1 µg to 5 mg per dose, more preferably from about 10 µg to 2 mg per dose, more preferably from about 50 µg to about 1 mg per dose, and more preferably from 100 µg to about 500 µg per dose. Preferably the therapeutically effective dose is a single dose. Also preferably administration of the vaccine to the mammal produces no side effects such as, for example, no fever or inflammation at the site of administration.

Another embodiment of the invention comprises methods for manufacture of a vaccine that treats or prevents an infection caused by one or more of *B. pertussis, B. parapertussis* or a serotype or strain of *B. pertussis* or *B. parapertussis* comprising combining a detoxified *pertussis* toxin protein, an enzyme treated LPS, and a detoxified adenylate cyclase protein. Preferably the composition comprises a pharmaceutically acceptable carrier and/or an adjuvant.

Other embodiments and advantages of the invention are set forth in part in the description, which follows, and in part, may be obvious from this description, or may be learned from the practice of the invention.

DESCRIPTION OF THE DRAWINGS

FIG. 1. Schematic representation of the detoxification of *pertussis*.

DESCRIPTION OF THE INVENTION

Current acellular *pertussis* preparations are difficult to make and do not consistently elicit an immune response strong enough to protect vaccinated subjects. This is believed to be due to the removal of innate danger signals present in the whole cell vaccine, but absent in the highly purified acellular preparation. On the flip side, whole cell *pertussis* vaccine is reactogenic and therefore not preferred for pediatric use. A large part of the reactogenicity and toxicity residue in the *pertussis* toxins encoded by Pertussis Toxin (PT) and cyclase as well as by the TLR4 agonist LPS. Both cyclase and LPS can be made into adjuvants that are safe by disrupting the adenylate cyclase activity of cyclase and by removing phosphate and sugars from the LPS yielding an MPL like molecule.

It has been surprisingly discovered that by engineering a *pertussis* strain currently utilized as a whole-cell vaccine, the undesirable effects from the quality immune effects a whole cell vaccine can be decoupled. Decoupling is performed by detoxifying three components namely *pertussis* toxin (PT), *pertussis* lipopolysaccharide (P-LPS), and *pertussis* adenylate cyclase toxin (P-ACT).

Accordingly, one embodiment of the invention is directed to a vaccine for the treatment or prevention of infection by *B. pertussis* comprising detoxified *pertussis* toxin (PT), detoxified *pertussis* lipopolysaccharide (P-LPS), and detoxified *pertussis* adenylate cyclase toxin (P-ACT) PT is released from *B. pertussis* in an inactive form and binds to a cell membrane receptor. From the receptor, PT is adsorbed into endosomes and undergoes a retrograde transport which activates the A subunit, that than catalyzes ADP-ribosylation of the $\alpha_i$ subunits of the heterotrimeric G protein. G protein is than prevented from interacting with its membrane receptor and thereby prevent intracellular communication. The Gi subunits remain locked in an inactive state unable to inhibit adenylyl cyclase activity. This results in an increased cellular concentration of cAMP that thus prevents biological signaling, causing a release of insulin and hypoglycemia. PT is therefore a preferred component of acellular vaccines.

Another embodiment of the invention is directed to methods of treating or preventing an infection comprising administering a therapeutically effective amount of the vaccine of the invention to a mammal. Vaccines of the invention may be administered to patients in need in a variety of routes such as, for example, via injection (e.g., intramuscular, intravenous), orally by tablets, pills or liquids, nasally by spray or another route known and available to those skilled in the art. Vaccines of the invention may also include a pharmaceutically acceptable carrier such as, for example, water, glycerol, alcohol, propylene glycol, fatty alcohols, triglycerides, fatty acid esters, mineral oils, liquid petrolatum, isopropylpalmitate, polyethylene ethanol, polyoxyethylene monolauriater, sodium lauryl sulfate, an anti-oxidant, a humectant, a viscosity stabilizer or modifier, a colorant or a flavoring agent. Preferably the vaccine of the invention is non-toxic at the concentration utilized, and contains no adhesins, such as *B. pertussis* adhesins.

Detoxifying PT

PT dissociates into two parts in the endoplasmic reticulum (ER): the enzymatically active A subunit (S1) and the cell-binding B subunit. The two subunits are separated by proteolytic cleavage. The B subunit will undergo ubiquitin-dependent degradation by the 26S proteasome. However, the A subunit lacks lysine residues, which are essential for ubiquitin-dependent degradation. Therefore, PT subunit A will not be metabolized like most other proteins. PT is heat-stable and protease-resistant, but once the A and B are separated, these properties change. The B subunit will stay heat-stable at temperatures up to about 60° C., but it is susceptible to protein degradation. PT subunit A, on the other hand, is less susceptible to ubiquitin-dependent degradation, but is unstable at temperature of about 37° C. and above. This facilitates unfolding of the protein in the ER and tricks the cell into transporting the A subunit to the cytosol, where normally unfolded proteins will be marked for degradation. So, the unfolded conformation will stimulate the ERAD-mediated translocation of PT A into the cytosol. Once in the cytosol, it can bind to NAD and form a stable, folded protein again. Being thermally unstable is also the Achilles heel of PT subunit A. As always, there is equilibrium between the folded and unfolded states. When the protein is unfolded, it is susceptible to degradation by the 20S proteasome, which can degrade only unfolded proteins.

There are a number of mutations that result in detoxified PT while still allowing the production of antibodies responsive to native PT. *Pertussis* toxin has five subunits, S1-S5, and most proposed mutations focus on S1-S3. Mutations in the catalytic subunit S1 disable the ADP-ribosylation activity of PT while leaving the structure intact and include Arg$^9$→Lys$^9$ and Glu$^{129}$→Gly$^{129}$ (see e.g., U.S. Pat. No. 7,169,399, which is incorporated by reference). The remaining four subunits of PT constitute the B-oligomer responsible for binding cells prior to their invasion. Proposed mutations or deletions to the S2 and/or S3 subunits include some combination of Asn$^{105}$, Tyr$^{102}$, or Tyr$^{102-103}$ of S2 and/or Lys$^{10}$, Tyr$^{92}$, Lys$^{93}$, Lys$^{93}$, or Tyr$^{102-103}$ of S3. These mutations hinder the ability of PT to bind cells while still enabling the generation of anti-PT antibodies.

Chromosomal integration of mutations involves two major steps—plasmid transfer via bacterial conjugation from transformed *E. coli* followed by chromosomal integration via homologous recombination. There are a number of recombinant strategies for accomplishing these steps, all well-known and commercially available. A preferred method involves conjugative transfer using an *E. coli* strain (e.g. SM10 as the conduit into *B. pertussis*) and the Life Technologies TALEN system for homologous recombination integration into the chromosomal DNA.

Modifying P-LPS to Remove Reactogenicity

To detoxify LPS, phosphatase (e.g. alkaline phosphatase, Antarctic phosphatase, lambda protein phosphatase) is used to dephosphorylate the core-oligosaccharide of LPS, which results in an effective means of detoxification of the compound. Upon induced lysis of *B. pertussis*, samples are treated with these phosphatases before performing cytotoxicity assays to identify preferred enzymes. Plasmids formed will trigger enzyme expression and apoptosis upon induction. The designer genes are integrated into the *B. pertussis* chromosomal DNA as described above. This allow a production process whereby cells are cultured to saturation, the phosphatase is induced, and upon lysis generates a mono- and aphosphoryl-LPS/Lipid A that retains adjuvant activity without toxic effects. A similar strategy is applied using a deacylases that remove one or more acyl chains from the Lipid A core thereby reducing or removing innate stimulatory capacity.

Replacing P-ACT with a Detoxified Version

As with PT, changes in P-ACT can be modified to generate a non-toxic version of this protein. The dipeptide leu-gln is inserted between amino acids 188 and 189 of the native P-ACT, which detoxifies P-ACT. Alternatively, amino acid residues 1188 to 1281 of the CyaA protein of *B. pertussis* may be mutated to create a vector wherein either modification is used in the same manner as described in herein; to knock out native P-ACT to be replaced with a non-toxic version that maintains adjuvanticity as well as the antigen's immunogenicity.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method of treating or preventing an infection caused by one or more of *B. pertussis, B. parapertussis* or a serotype or strain of *B. pertussis* or *B. parapertussis*, in a mammal comprising administering to the mammal a therapeutically effective dose of a vaccine, wherein the vaccine comprises a detoxified *pertussis* toxin protein; an enzyme treated *pertussis* detoxified LPS; and a detoxified *pertussis* adenylate cyclase protein.

2. The method of claim 1, wherein administering is via injection, intramuscular injection, intravenous injection, oral administration, nasal administration, or a combination thereof.

3. The method of claim 1, wherein the vaccine is a liquid, a tablet, a pill or a spray.

4. The method of claim 1, wherein the therapeutically effective dose is an amount of vaccine which produces an immune response in the mammal that is protective against and/or treats the infection.

5. The method of claim 4, wherein the amount of vaccine is from about 1 μg to 1 mg per dose.

6. The method of claim 1, wherein the therapeutically effective dose is a single dose.

7. The method of claim 1, wherein administration of the vaccine to the mammal produces no side effects.

8. The method of claim 7, wherein the no side effects comprise the absence of a fever or an inflammation at the site of administration.

9. The method of claim 1, wherein the vaccine is protective against and/or treats an infection caused by multiple serotypes and/or strains of *B. pertussis* and/or *B. parapertussis*.

10. The method of claim 1, wherein the detoxified *pertussis* protein contains a mutation in one or more of subunits S1-S5 of *B. pertussis*.

11. The method of claim 10, wherein the mutation comprises a substitution in S1 of glutamic acid for glycine at amino acid position 129 and a substitution of arginine for lysine at amino acid position 9.

12. The method of claim 1, wherein enzyme treated LPS comprises LPS treated with one or more alkaline phosphatases or one or more deacylases.

13. The method of claim 12, wherein the one or more phosphorylaese comprise Antarctic phosphatase or lambda protein phosphatase.

14. The method of claim 1, wherein the detoxified adenylate cyclase protein comprised a dipeptide inserted between amino acids 188 and 189 of native *pertussis* adenylate cyclase protein.

15. A method of treating or preventing infections caused by multiple strains and/or serotypes of *B. pertussis* and *B. parapertussis* in a mammal comprising administering to the mammal a therapeutically effective dose of a vaccine, wherein the vaccine comprises a detoxified *pertussis* toxin protein wherein the detoxified *pertussis* protein contains a mutation in one or more of subunits S1-S5 of *B. pertussis*; a *pertussis* detoxified LPS that has been treated with one or more alkaline phosphatases or one or more deacylases; and a detoxified *pertussis* adenylate cyclase protein that contains one or more mutations.

16. The method of claim 15, wherein the one or more phosphorylaese comprise Antarctic phosphatase or lambda protein phosphatase.

17. The method of claim 15, wherein the mutation comprises a substitution in S1 of glutamic acid for glycine at amino acid position 129 and a substitution of arginine for lysine at amino acid position 9.

18. The method of claim 1, wherein the detoxified adenylate cyclase protein comprised a dipeptide inserted between amino acids 188 and 189 of native *pertussis* adenylate cyclase protein.

\* \* \* \* \*